(12) United States Patent
Lee

(10) Patent No.: US 7,624,626 B2
(45) Date of Patent: Dec. 1, 2009

(54) DYNAMIC FLOW LIQUID CHROMATOGRAPHY

(75) Inventor: Dlan Y. Lee, Hockessin, DE (US)

(73) Assignee: Aim Research Co., Hockessin, DE (US)

( * ) Notice: Subject to any disclaimer, the term of this patent is extended or adjusted under 35 U.S.C. 154(b) by 332 days.

(21) Appl. No.: 11/550,946

(22) Filed: Oct. 19, 2006

(65) Prior Publication Data

US 2007/0108126 A1     May 17, 2007

Related U.S. Application Data

(60) Provisional application No. 60/737,428, filed on Nov. 17, 2005.

(51) Int. Cl.
     *B01D 15/08*     (2006.01)
     *B01D 15/18*     (2006.01)
     *G01N 30/84*     (2006.01)

(52) U.S. Cl. ............... 73/61.56; 73/61.52; 73/61.55; 210/101; 210/635; 210/656

(58) Field of Classification Search ........... 73/61.52, 73/61.53, 61.55, 61.56; 210/101, 635, 656
See application file for complete search history.

(56) References Cited

U.S. PATENT DOCUMENTS

| | | | |
|---|---|---|---|
| 5,240,577 A | 8/1993 | Jorgenson et al. | |
| 6,139,734 A | 10/2000 | Settlage et al. | |
| 6,402,946 B1 | 6/2002 | Spraul et al. | |
| 6,546,786 B2 | 4/2003 | Lee et al. | |
| 6,858,435 B2 | 2/2005 | Chervet et al. | |
| 2002/0072126 A1* | 6/2002 | Chervet et al. | 436/161 |
| 2007/0183928 A1* | 8/2007 | Neyer et al. | 422/70 |

FOREIGN PATENT DOCUMENTS

EP     0495255 A1     7/1992

OTHER PUBLICATIONS

Rabbany, S. Y. et al., "Trace Detection of Explosives uisng a Membrane-Based Displacement Immunoassay", Journal of Immunological Methods, vol. 246, 2000, p. 69-77.*
Macko et al. "Pressure Effects In Hplc: Influence Of Pressure And Pressure Changes On Peak Shape, Base Line, And Retention Volume In Hplc Separations," J Liq Chromatography Rel Tech (2001) 24(9):1275-1293.
Nassar et al., "On-line liquid chromatography-accurate radioisotope counting coupled with a radioactivity detector and mass spectrometer for metabolite identification in drug discovery and development.," Anal Chem (2003) 75(4):785-790.
Abersold, R., et al., Mass spectrometry in proteomics, Chem Rev. Feb. 2001;101(2):269-95.

(Continued)

*Primary Examiner*—Daniel S Larkin
(74) *Attorney, Agent, or Firm*—Paul K. Legaard

(57) ABSTRACT

The present invention provides apparatus and methods for detection of an analyte in liquid chromatography with increased detection sensitivity and signal resolution.

16 Claims, 4 Drawing Sheets

OTHER PUBLICATIONS

Davis, M. T., et al., A microscale electrospray interface for on-line, capillary liquid chromatography/tandem mass spectrometry of complex peptide mixtures, Anal Chem. Dec. 15, 1995;67(24):4549-56.

Davis, M. T., et al., Variable flow liquid chromatography-tandem mass spectrometry and the comprehensive analysis of complex protein digest mixtures, J. Amer Soc Mass Spectrom, 1997;8:1059-69.

Martin, S. E., et al., Subfemtomole MS and MS/MS peptide sequence analysis using nano-HPLC micro-ESI fourier transform ion cyclotron resonance mass spectrometry, Anal Chem. Sep. 15, 2000;72(18):4266-74.

* cited by examiner

DYNAMIC FLOW LIQUID CHROMATOGRAPHY

CROSS-REFERENCE TO RELATED APPLICATIONS

This application claims priority to U.S. provisional application Ser. No. 60/737,428 filed Nov. 17, 2005, which is incorporated herein by reference in its entirety.

FIELD OF THE INVENTION

The present invention is directed, in part, to an apparatus and methods for radioactivity detection in liquid chromatography which increase detection sensitivity and signal resolution.

BACKGROUND OF THE INVENTION

High pressure liquid chromatography (HPLC) is widely considered to be a technique mainly for biotechnological, biomedical, and biochemical research as well as for the pharmaceutical industry, these fields currently comprise only about 50% of HPLC users. However, HPLC is currently used by a variety of fields including cosmetics, energy, food, and environmental industries.

Prior to the 1970's, few reliable chromatographic methods were commercially available to laboratory scientists. During the 1970's, most chemical separations were carried out using a variety of techniques including open-column chromatography, paper chromatography, and thin-layer chromatography. However, these chromatographic techniques were inadequate for quantification of compounds and resolution between similar compounds. During this time, pressure liquid chromatography began to be used to decrease flowthrough time, thus reducing purification times of compounds being isolated by column chromatography. However, flow rates were inconsistent, and the question of whether it was better to have constant flow rate or constant pressure was debated.

HPLC was developed in the mid-1970's and quickly improved with the development of column packing materials and the additional convenience of on-line detectors. In general, HPLC is used to separate components of a mixture by using a variety of chemical interactions between the substance being analyzed (analyte) and the chromatography column. The analyte is forced through a column of the stationary phase by introducing a liquid at high pressure. Use of pressure prevents the components from diffusing within the column, leading to improved resolution in the resulting chromatogram. Solvents used include any miscible combination of water or various organic liquids (the most common are methanol and acetonitrile). Water may contain buffers or salts to assist in the separation of the analyte components, or compounds such as trifluoroacetic acid.

In the late 1970's, new methods including reverse phase liquid chromatography allowed for improved separation between very similar compounds, and by the 1980's HPLC was commonly used for the separation of chemical compounds. Modern HPLC has many applications including separation, identification, purification, and quantification of various compounds. Computers and automation have added to the convenience of HPLC, and the past few decades have seen a vast undertaking in the development of the microcolumns and other specialized columns which have yielded improved results.

HPLC typically comprises a pump, column, and a detector. According to Van Deep curve, for a given LC column demension and packings, there is an optimum flowrate to achieve the maximum separation efficiency or plate number.

Sensitivity and resolution are the most important indicators in chromatography. Sensitivity depends on several factors. One of the most important factors is the residence time (or Time of Flight. TOF) of a peak passing through the detector. Resolution also depends on the duration the peak passing through the detector. Therefore, the detector's flow cell volume is selected to balance between resolution and sensitivity requirements. If the flow cell is too large, the sensitivity increases, however, the resolution will be sacrificed. If the flow cell is too small, then the resolution increases, but the sensitivity decreases.

Simply slowing the LC flowrate will deviate from optimum separation efficiency. Furthermore, under normal settings, slowing down HPLC flowrate would result in lower pressure in column.

Pressure is one of the most important factors in HPLC separation. Interruption of pressure during the separation would result in poor separation performance and an unusual detector response (Macko et al., J. Liq. Chromtography Rel. Tech., 2001, 24, 1275-1293).

However, the traditional methods do not have a mechanism to prevent the column pressure drop when LC flowrate change occurs.

The conflict between sensitivity and resolution is apparent for radioactivity detection in HPLC. In order to detect radioactivity from HPLC, a flow cell with either a solid or liquid scintillator is used. In case of a liquid cell, a separate pump is used to deliver liquid scintillator to be used with eluate from HPLC and the mixture flows through the flow cell, normally made of a coiled transparent tubing. When using a solid cell, the eluate pass through the flow cell packed with solid scintillator particles.

To detect radioactivity from HPLC, a flow cell with either a solid or liquid scintillator is used. In case of a liquid cell, a separate pump is used to deliver liquid scintillator to be used with eluate from HPLC and the mixture flows through the flow cell, normally made of a coiled transparent tubing. When using a solid cell, the eluate pass through the flow cell packed with solid scintillator particles. The conflict between detection sensitivity and signal resolution is also fundamental to radioactivity detection in HPLC.

Many advances in HPLC technology have been made in the past few decades, however, currently available detectors are unable to effectively detect/process the eluting peaks, especially when the peak width is getting smaller with faster separation in HPLC columns. The time a peak flows through a flow cell is called TOF (Time-of-Flight). TOF depends on several parameters: LC flowrate, agent flowrate, and cell volume. For example, under normal circumstance when LC flowrate is 1 ml/min, volume-adding component flows at 3:1 ratio, a flow cell of 500 µl volume is used to obtain optimum sensitivity with good resolution. This setting will result in a TOF of $(500/(1000/(1+3))\times 60)=7.5$ seconds. The TOF is very important because TOF affects the peak resolution and detection sensitivity. If TOF is too long, then the peaks can not be resolved well and the separation is compromised. In the other words, if TOF is too long, two narrowly resolved peaks might end up residing in one cell volume so that they are detected as one merged peak. On the other hand, when TOF is too small, the radioactivity detection sensitivity degrades since the quantity of radioactivity detection depends on the counting time or TOF. For radioactivity detection, the longer the counting time (or TOF), the better accuracy the detection is. Under these conditions, all the peaks will be counted for the same or similar TOF and the sensitivity for smaller peaks will be low.

Smaller peaks can not be detected and missed due to the poor sensitivity. In order to achieve high sensitivity of radioactivity detection, traditionally LC fractions are collected for off-line counting for longer period of time. Recently, a on-line stop-flow technique is being used to increase the radioactivity detection sensitivity (U.S. Pat. No. 6,546,786; and Nassar et al., Anal. Chem., 2003, 75, 785-790). Those methods result in longer analytical time. Thus, there is a need for a better system that can preserve optimum separation of analyte components and provide a longer time for detector analysis to simultaneously increase detection sensitivity and signal resolution.

SUMMARY OF THE INVENTION

The present invention provides an apparatus comprising a pump, a separator in fluid communication with the pump, a pressure restrictor in fluid communication with the separator, a mixing component in fluid communication the pressure restrictor and a volume-adding component, and a detector in fluid communication with the mixing component. In some embodiments, the pump further comprises a mobile phase.

In some embodiments, the separator is a liquid chromatography column, a high pressure liquid chromatography column, a capillary column, a nano liquid chromatography column, or a reverse phase high pressure liquid chromatography column, or any subgroup thereof. In some embodiments, the pressure restrictor is a needle valve. In some embodiments, the mixing component is a mixing tee. In some embodiments, the volume-adding component is a second pump.

In some embodiments, the present invention further comprises a detector in fluid communication with the pressure restrictor. The detector is a mass spectrometer, a nuclear magnetic resonance detector, a radioactivity detector, an ultraviolet detector, or an electrochemical detector, or any subgroup thereof. In some embodiments, the detector is a radioactivity detector which comprises a liquid cell or a solid cell.

In some embodiments, the present invention further comprises a controller in electronic communication with the detector, pressure restrictor, and volume-adding component. In some embodiments, the controller is a microprocessor and/or computer software.

In some embodiments, the present invention further comprises a stepper motor attached to the pressure restrictor. The stepper motor is optionally in electronic communication with the controller. In some embodiments, the stepper motor activates or de-activates the pressure restrictor.

The present invention also provides methods for increasing resolution of an analyte comprising passing a mobile phase comprising the analyte from a separator to a detector at a first detector flow rate when a signal from the detector is less than a preset threshold, wherein the separator and detector are in fluid communication with each other, and increasing the first detector flow rate of the mobile phase through the detector to a second detector flow rate when the signal from the detector is greater than the preset threshold. The separator, detector, and second detector can be any of those described herein. In some embodiments, the second detector flow rate can be about 100%, 500%, or 1000% faster than the first detector flow rate.

In some embodiments, the first detector flow rate is increased to the second detector flow rate by activating a volume-adding component, wherein the volume-adding component is in fluid communication with the detector and is located between the detector and the separator. The activated volume-adding component introduces an agent into the mobile phase passing into the detector. In some embodiments, the volume-adding component is a second pump. In some embodiments, the agent is a second mobile phase, a scintillation fluid, or an organic solvent.

In some embodiments, increasing the first detector flow rate to the second detector flow rate is carried out by activating a pump, which is in fluid communication with the separator. The pump introduces more mobile phase passing into the separator, thus allowing an increased flow of mobile phase from the separator to the detector.

In some embodiments, the first detector flow rate is increased to the second detector flow rate by the combination of: activating a volume-adding component, wherein the volume-adding component is in fluid communication with the detector and is located between the detector and the separator, whereby the activated volume-adding component introduces an agent into the mobile phase passing into the detector; and activating a pump, which is in fluid communication with the separator, to allow an increased flow of mobile phase into the separator and to the detector.

In some embodiments, the methods further comprise decreasing the second detector flow rate back to about the first detector flow rate when the signal from the detector is less than a preset threshold. In some embodiments, the second detector flow rate is decreased back to about the first detector flow rate by deactivating a volume-adding component, wherein the volume-adding component is in fluid communication with the detector and is located between the detector and the separator, whereby the deactivated volume-adding component introduces less agent into the mobile phase passing into the detector. In some embodiments, the second detector flow rate is decreased back to about the first detector flow rate by deactivating a pump, which is in fluid communication with the separator, to allow decreased flow of mobile phase into the separator and to the detector.

In some embodiments, a controller, which is in electronic communication with the detector and volume-adding component, activates or deactivates the volume-adding component. In some embodiments, a controller, which is in electronic communication with the detector and pump, activates or deactivates the pump. In some embodiments, a controller, which is in electronic communication with the detector, pump, second pump, and needle valve, activates or deactivates the pump, second pump and/or needle valve.

The present invention also provides methods for increasing sensitivity of detection of an analyte comprising passing a mobile phase comprising the analyte from a separator to a detector at a first detector flow rate, wherein the separator and detector are in fluid communication with each other, and decreasing the first detector flow rate of the mobile phase through the detector to a second detector flow rate when the signal from the detector is less than the preset threshold or when reaching a predetermined time. In some embodiments, the analyte, separator, and detector can be any of those described herein.

In some embodiments the first detector flow rate is decreased to the second detector flow rate by any combination of: (i) deactivating a volume-adding component, wherein the volume-adding component is in fluid communication with the detector and is located between the detector and the separator, whereby the activated volume-adding component reduces the volume of an agent into the mobile phase passing into the detector; (ii) deactivating a pressure restrictor to allow a decreased flow of mobile phase from the separator to the detector, wherein the pressure restrictor is in fluid communication with the detector and separator; and (iii) deactivating a pump in fluid communication with the separator to allow a decreased flow of mobile phase into the separator and to the detector. In some embodiments, the pressure in the separator remains substantially steady after the first restrictor flow rate is decreased to the second restrictor flow rate. In some embodiments, the second detector flow rate is at least about 100%, 1000%, or 20,000% slower than the first detector flow rate. In some embodiments, the pressure restrictor is a needle valve. In some embodiments, the volume-adding component is a second pump. In some embodiments, the agent is a second mobile phase, a scintillation fluid, or an organic solvent.

In some embodiments, a controller, which is in electronic communication with the detector and volume-adding component, deactivates the volume-adding component. In some embodiments, a controller, which is in electronic communication with the detector and pressure restrictor, deactivates the pressure restrictor. In some embodiments, a controller, which is in electronic communication with the detector and pump, deactivates the pump. In some embodiments, a controller, which is in electronic communication with the detector, pump, and the second pump, deactivates the second pump, pump, and/or the needle valve.

DESCRIPTION OF EMBODIMENTS

Figure 1:
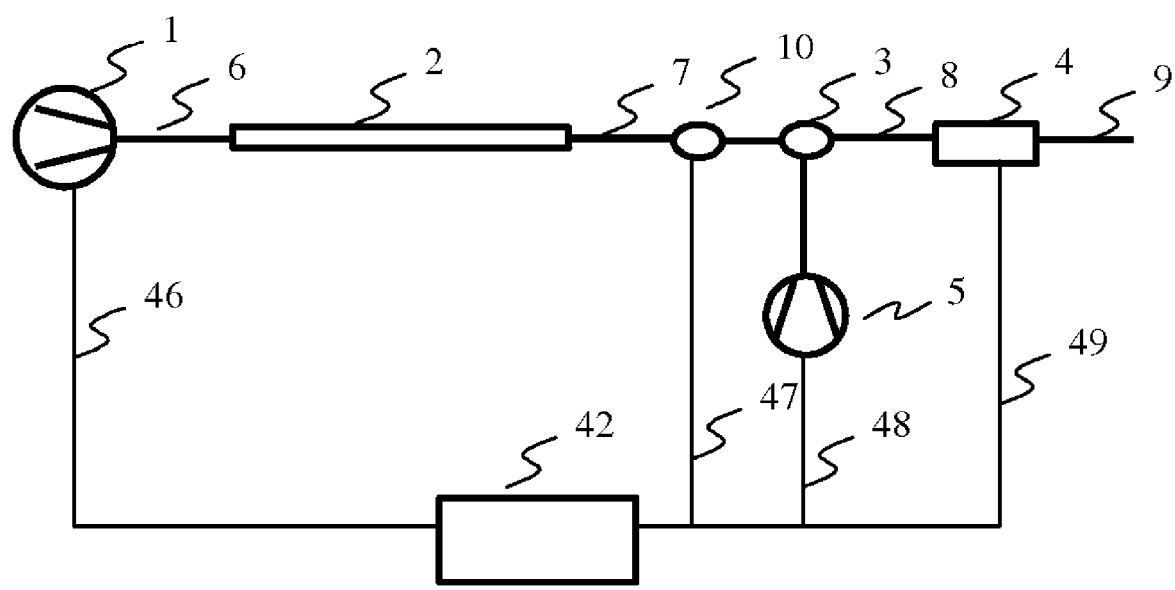
FIG. 1 illustrates a LC apparatus with a pressure restrictor positioned after the separator.

The present invention provides apparatus for detecting an analyte while maintaining pressure. FIG. 1 illustrates a representative flow control system for controlling LC flow and detecting an radioactive analyte using a liquid cell in prior arts. The apparatus comprises a pump (1), a separator (2), a pressure restrictor (10), a mixing component (3), a detector (4), and a volume-adding component (5).

In some embodiments of the present invention, the pump (1) is of the type known to one of ordinary skill in the art. Any pump that can force a mobile phase through a separator (2) can be used. The pump (1) is in fluid communication with the separator (2).

In some embodiments of the present invention, the separator (2) is a liquid chromatography column, a high pressure liquid chromatography column, a capillary column, a nano liquid chromatography column, or a reverse phase high pressure liquid chromatography column, or any subgroup thereof. The separator (2) is in fluid communication via connector (6) with the pump (1). An analyte to be separated can be present within the mobile phase within the pump (1) or can be delivered to the separator (2) via a sample injector (not shown). The separation of analyte components in the separator (2) is governed by van Deemter theory; for a column with particular dimensions and characteristics, an optimum flow rate can be predicted. Some embodiments of the present invention further comprise more than one separator (2). Separator (2) can be a stainless tube packed with fine particles (e.g., 5 µm in diameter) which have different surface characteristics.

Referring to FIG. 1, the pressure restrictor (10) is in fluid communication via connector (7) with the separator (2). In some embodiments, the pressure restrictor (10) is a needle valve. In some embodiments, the pressure restrictor (10) is an On/Off needle valve. A suitable On/Off valve can be obtained from Valco (part number: ASFVO, Houston, Tex.).

The mixing component (3) is in fluid communication with the pressure restrictor (10) and with the volume-adding component (5). In some embodiments, the mixing component (3) is a mixing tee. Any commercially available mixing tee can be used in the apparatus described herein.

The volume-adding component (5) is any component that can add volume to the detector, such as, for example, a second pump or a syringe. Any commercially available pump or syringe can be used in the apparatus described herein. In some embodiments, the volume-adding component (5) can be optionally located between the detector (4) and the separator (2).

The apparatus further comprises a detector (4) in fluid communication via connector (8) with the pressure restrictor (10). In some embodiments, the detector (4) is a mass spectrometer, a nuclear magnetic resonance detector, a radioactivity detector, an ultraviolet detector, or an electrochemical detector, or any subgroup thereof. In some embodiments, the detector (4) is a radioactivity detector which comprises a liquid cell or a solid cell. Connectors (6), (7), (8), and (9) can be any type of tubing, such as stainless steel tubing, compatible with LC which can pass fluid from one element within the system to another element within the system.

In some embodiments, the apparatus further comprises a controller (42) in electronic communication via connectors (46), (47), (48), and (49) respectively, with the pump (1), pressure restrictor (10), detector (4), and volume-adding component (5). In some embodiments, the controller (42) is a microprocessor and/or computer software.

According to some embodiments, the apparatus further comprises a stepper motor (not shown) attached to the pressure restrictor (10), wherein the stepper motor is optionally in electronic communication with the controller (42). In some embodiments, the stepper motor is attached to the handle (not shown) of the pressure restrictor (10). The stepper motor activates or de-activates the pressure restrictor (10). The fine adjustment of the pressure restrictor (10) is accomplished by the use of the stepper motor which is programmed to adjust the opening.

The embodiments of the apparatus described above can be combined in any manner. Thus, features of one embodiment can be combined with features from any other embodiment. For example, the embodiments described above can be combined in a manner to produce an apparatus comprising: a pump (1); a separator (2) in fluid communication with the pump (1), wherein the separator is a liquid chromatography column, a high pressure liquid chromatography column, a capillary column, a nano liquid chromatography column, or a reverse phase high pressure liquid chromatography column; a pressure restrictor (10) in fluid communication with the separator (2), wherein the pressure restrictor (10) is a needle valve; a mixing component (3) in fluid communication the pressure restrictor (10) and a volume-adding component (5), wherein the mixing component (3) is a mixing tee, and wherein the volume-adding component (5) is a second pump; and a detector (4) in fluid communication with the pressure restrictor (10), wherein the detector (4) is a mass spectrometer, a nuclear magnetic resonance detector, a radioactivity detector, an ultraviolet detector, or an electrochemical detector. Such an apparatus may further comprise a controller (42) in electronic communication with the pump (1), pressure restrictor (10), and detector (4), wherein the controller (42) is a microprocessor and/or computer software. Such an apparatus may further comprise a stepper motor attached to the pressure restrictor (10), wherein the stepper motor is in electronic communication with the controller (42).

The embodiments described above can also be combined in a manner to produce an apparatus comprising, for example: a pump (1); a separator (2) in fluid communication with the pump (1), wherein the separator (2) is a liquid chromatography column, a high pressure liquid chromatography column, a capillary column, a nano liquid chromatography column, or a reverse phase high pressure liquid chromatography column; a pressure restrictor (10) in fluid communication with the separator (2), wherein the pressure restrictor (10) is a needle valve; a mixing component (3) in fluid communication the pressure restrictor (10) and a volume-adding component (5), wherein the mixing component (3) is a mixing tee, and wherein the volume-adding component (5) is a second pump; a detector (4) in fluid communication with the pressure restrictor (10), wherein the detector (4) is a mass spectrometer, a nuclear magnetic resonance detector, a radioactivity detector, an ultraviolet detector, or an electrochemical detector; and a controller (42) in electronic communication with the pump (1), pressure restrictor (10), and detector (4), wherein the controller (42) is a microprocessor and/or computer software. Such an apparatus may further comprise a stepper motor attached to the pressure restrictor (10), wherein the stepper motor is in electronic communication with the controller (42).

The present invention also provides methods for increasing resolution of an analyte comprising: passing a mobile phase comprising the analyte to a separator (2); passing the mobile phase from a separator (2) to a detector (4) at a first detector flow rate when a signal from the detector (4) is less than a preset threshold, wherein the separator (2) and detector (4) are in fluid communication with each other; and increasing the first detector flow rate of the mobile phase through the detector (4) to a second detector flow rate when the signal from the detector (4) is greater than the present threshold. The separator (2) and detector (4) can be any of those described herein. The second detector flow rate is measured by a flow sensor (not shown) located in an appropriate position. Flow sensors can be generally located throughout the apparatus to measure particular desired flow rates.

In some embodiments, the mobile phase is a scintillation fluid, an organic solvent, or the like. The analyte(s) can be present in the mobile phase or can be introduced into the mobile phase by a sample injector (not shown) prior to being passed to the separator (2). In addition, the analyte(s) being detected can be a single analyte or a plurality of analytes. Further, the analyte can be any molecule, compound, ion, or the like whose detection is sought. If a liquid cell is used, the volume-adding component (5) will pump liquid scintillation cocktail at certain flowrate to be mixed with elute at mixing component (3) and the mixture flows into the liquid cell inside the detector (4). When a solid cell is used, volume-adding component (5) can be used to pump organic solvents to control the TOF (time of flight) of analytes flowing through the solid cell.

The mobile phase comprising the analyte is passed to a separator (2) at a first pump flow rate from a pump (1). The first pump rate can be from about 0.1 ml/min to about 10 ml/min, from about 0.5 ml/min to about 5 ml/min, from about 1 ml/min to about 2 ml/min, or about 1 ml/min. As used in this context, the term "about" means±5% of the value it modifies. The mobile phase is then passed from the separator (2) to a detector (4) at a first detector flow rate, wherein the detector (4) is in fluid communication with the separator (2), as described above. The first detector flow rate can be from about 0.1 ml/min to about 10 ml/min, from about 0.5 ml/min to about 5 ml/min, from about 1 ml/min to about 2 ml/min, or about 1 ml/min. As used in this context, the term "about" means±5% of the value it modifies.

When the signal from the detector (4) is greater than the preset threshold, the first detector flow rate is increased to a second detector flow rate. In some embodiments, the second detector flow rate is at least about 100%, at least about 500%, or at least about 1000% times faster than the first detector flow rate. As used in this context, the term "about" means±5% of the value it modifies. In some embodiments, the preset threshold is a predetermined value such as a particular radioactivity value desired by the user. In some embodiments, the preset threshold determines the beginning of the peak from the analyte.

According to some embodiments, increasing the first detector flow rate to the second detector flow rate when the signal from the detector (4) is greater than the preset threshold is affected by activating the pump (1) to allow an increased flow of mobile phase into the separator (2) and to the detector (4). In some embodiments, when the signal from the detector (4) is greater than the preset threshold, the detector (4) signals a controller (42), which is in electronic communication with the detector (4), as described above, whereby the controller (42) signals the pump (1) to introduce more mobile phase into the separator, thereby increasing the first detector flow rate to the second detector flow rate.

In some embodiments, increasing the first detector flow rate to the second detector flow rate when the signal from the detector (4) is greater than the preset threshold is affected by activating the volume-adding component (5). In some embodiments, the volume-adding component (5) is a second pump. In some embodiments, when the signal from the detector (4) is greater than the preset threshold, the detector (4) signals a controller (42), which is in electronic communication with the detector (4), as described above, whereby the controller (42) signals the volume-adding component (5) to introduce an agent into the mobile phase, thereby increasing the first detector flow rate to the second detector flow rate. In some embodiments, the agent is a second mobile phase, a scintillation fluid, or an organic solvent. The controller (42) can be any controller described above.

In some embodiments, increasing the first detector flow rate to the second detector flow rate when the signal from the detector (4) is greater than the preset threshold is affected by activating a pressure restrictor (10) such as a needle valve to allow an increased flow of mobile phase from the separator (2) to the detector (4), wherein the needle valve is in fluid communication with the detector (4) and separator (2).

In some embodiments, the first detector flow rate is increased to the second detector flow rate by any combination of: activating the volume-adding component (5), wherein the volume-adding component (5) is in fluid communication with the detector (4) and is located between the detector (4) and the separator (2), whereby the activated volume-adding component (5) introduces an agent into the mobile phase passing into the detector (4); activating the pump (1) to allow an increased flow of mobile phase into the separator (2) and to the detector (4); and activating a pressure restrictor (10) such as a needle valve to allow an increased flow of mobile phase from the separator (2) to the detector (4), wherein the needle valve is in fluid communication with the detector (4) and separator (2).

In some embodiments, the methods further comprise decreasing the second detector flow rate back to about the first detector flow rate when the signal from the detector (4) becomes less than the preset threshold or a predetermined time. As used in this context, the term "about" means±50%, means±20%, means±10%, or means±5% of the first detector flow rate. In some embodiments, the preset threshold is a predetermined value such as a particular absorbance value. In some embodiments, the preset threshold determines the beginning of the peak from the analyte. In some embodiments, the preset threshold for increasing the first detector flow rate is identical to the preset threshold for decreasing the second detector flow rate.

According to some embodiments, decreasing the second detector flow rate back to about the first detector flow rate is affected by: deactivating a volume-adding component (5), whereby the activated volume-adding component (5) introduces less agent into the mobile phase passing into the detector (4); or by deactivating the pump (1) to allow decreased flow of mobile phase into the separator (2) and to the detector (4); or both.

In some embodiments, upon obtaining a signal less than the preset threshold, the detector (4) signals a controller (42), which is in electronic communication with the detector (4), as described above, whereby the controller (42): signals the volume-adding component (5) to introduce less agent into the mobile phase passing into the detector (4), thereby decreasing the second detector flow rate to about the first detector flow rate; or signals the pump (1) to introduce less mobile phase passing into the separator (2), thereby decreasing the second detector flow rate to about the first detector flow rate; or both. The controller (42) can be any controller described above. Deactivation of the volume-adding component (5) or pump (1), or both, as used herein, does not necessarily mean complete deactivation whereby the first detector flow rate is decreased to zero.

The embodiments of the methods described above can be combined in any manner. Thus, features from one embodiment can be combined with features from any other embodiment. For example, the embodiments described above can be combined in a manner to produce methods for increasing resolution of an analyte comprising: passing a mobile phase comprising the analyte from a separator (2) to a detector (4) at a first detector flow rate when a signal from the detector (4) is less than a preset threshold, wherein the separator (2) and detector (4) are in fluid communication with each other, and wherein the separator (2) is a liquid chromatography column, a high pressure liquid chromatography column, a capillary column, a nano liquid chromatography column, or a reverse phase high pressure liquid chromatography column, and wherein the detector (4) is a mass spectrometer, a nuclear magnetic resonance detector, a radioactivity detector, an ultraviolet detector, or an electrochemical detector; and increasing the first detector flow rate of the mobile phase through the detector (4) to a second detector flow rate when the signal from the detector (4) is greater than the preset threshold, wherein the increasing is carried out by: a) activating a volume-adding component (5) such as a second pump, wherein the second pump is in fluid communication with the detector (4) and is located between the detector (4) and the separator (2), whereby the activated second pump introduces an agent into the mobile phase passing into the detector (4); b) activating a pressure restrictor (10) such as a needle valve to allow an increased flow of mobile phase from the separator (2) to the detector (4), wherein the needle valve is in fluid communication with the detector (4) and separator (2); and c) activating the pump (1) to allow an increased flow of mobile phase into the separator (2) and to the detector (4); or any combination thereof.

The present invention also provides methods for increasing sensitivity of detection of an analyte comprising: passing a mobile phase comprising the analyte from a separator (2) to a detector (4) at a first detector flow rate, wherein the separator (2) and detector (4) are in fluid communication with each other; and decreasing the first detector flow rate of the mobile phase through the detector (4) to a second detector flow rate when the signal from the detector (4) is less than a present threshold or when reaching a predetermined time. The separator (2) and detector (4) can be any of those described herein. The pressure in the separator (2) remains substantially steady after the first restrictor flow rate is decreased to the second restrictor flow rate. In addition, the second detector flow rate is at least about 100% slower, at least about 1000% slower, or at least about 20,000% slower than the first detector flow rate. The second detector flow rate is measured by a flow sensor (not shown) located in an appropriate position. Flow sensors can be generally located throughout the apparatus to measure particular desired flow rates. As used in this context, the term "about" means±5% of the value it modifies. In some embodiments, the preset threshold is a predetermined value such as a particular absorbance value. In some embodiments, the preset threshold determines the beginning of the peak from the analyte.

In some embodiments, the mobile phase is a scintillation fluid, an organic solvent, or the like. The analyte(s) can be present in the mobile phase or can be introduced into the mobile phase by a sample injector prior to being passed to the separator (2). In addition, the analyte(s) being detected can be a single analyte or a plurality of analytes. Further, the analyte can be any molecule, compound, ion, or the like whose detection is sought.

In some embodiments, the mobile phase comprising the analyte is passed to a separator (2) at a first pump flow rate from a pump (1). The first pump rate can be from about 0.1 ml/min to about 10 ml/min, from about 0.5 ml/min to about 5 ml/min, from about 1 ml/min to about 2 ml/min, or about 1 ml/min. As used in this context, the term "about" means±5% of the value it modifies. The mobile phase is then passed from the separator (2) to a detector (4) at a first detector flow rate, wherein the detector (4) is in fluid communication with the separator (2), as described above. The first detector flow rate can be from about 0.1 ml/min to about 10 ml/min, from about 0.5 ml/min to about 5 ml/min, from about 1 ml/min to about 2 ml/min, or about 1 ml/min. As used in this context, the term "about" means±5% of the value it modifies.

According to some embodiments, decreasing the first detector flow rate to the second detector flow rate is affected by deactivating the pump (1) to allow decreased flow of mobile phase into the separator (2) and detector (4). In some embodiments, upon obtaining a signal less than the present threshold or when reaching a predetermined time, the detector (4) signals a controller (42), which is in electronic communication with the detector (4), as described above, whereby the controller (42) signals the pump (1) to allow decreased flow of mobile phase into the separator (2) and detector (4). The controller (42) can be any controller described above. Deactivation of the pump (1), as used herein, does not necessarily mean complete deactivation whereby the first pump flow rate is decreased to zero.

According to some embodiments, decreasing the first detector flow rate to a second detector flow rate is affected by deactivating a volume-adding component (5), whereby the activated volume-adding component (5) introduces less agent into the mobile phase passing into the detector. In some embodiments the volume-adding component (5) is a second pump. In some embodiments, the volume-adding component (5) is in fluid communication with the detector (4) and is located between the detector (4) and the separator (2). In some embodiments, upon obtaining a signal less than the preset threshold or when reaching a predetermined time, the detector (4) signals a controller (42), which is in electronic communication with the detector (4), as described above, whereby the controller (42) signals the volume-adding component (5) to introduce less agent into the mobile phase passing into the detector (4), thereby decreasing the first detector flow rate to the second detector flow rate. The controller (42) can be any controller described above. The volume-adding component (5) can be any volume-adding component described above. Deactivation of the volume-adding component (5), as used herein, does not necessarily mean complete deactivation whereby the first detector flow rate is decreased to zero.

According to some embodiments, decreasing the first detector flow rate to a second detector flow rate is affected by deactivating a pressure restrictor (10), whereby the activated pressure restrictor (10) allows a decreased flow of mobile phase from the separator (2) to the detector (4), wherein the pressure restrictor (10) is in fluid communication with the detector (4) and separator (2). In some embodiments of the methods described, the pressure restrictor (10) is a needle valve. In some embodiments the pressure restrictor (10) is an On/Off needle valve. A suitable On/Off valve can be obtained from Valco (part number: ASFVO, Houston, Tex.). In some embodiments, upon obtaining a signal less than the preset threshold or when reaching a predetermined time, the detector (4) signals a controller (42), which is in electronic communication with the detector (4), as described above, whereby the controller (42) signals the pressure restrictor (10) to introduce less mobile phase passing into the detector (4), thereby decreasing the first detector flow rate to the second detector flow rate. The controller (42) can be any controller described above. The pressure restrictor (10) can be any pressure restrictor described above. Deactivation of the pressure restrictor (10), as used herein, does not necessarily mean complete deactivation whereby the first detector flow rate is decreased to zero.

In some embodiments, the first detector flow rate is decreased to the second detector flow rate by any combination of: a) deactivating a volume-adding component (5), wherein the volume-adding component (5) is in fluid communication with the detector (4) and is located between the detector (4) and the separator (2), whereby the activated volume-adding component (5) reduces the volume of an agent into the mobile phase passing into the detector (4); b) deactivating a pressure restrictor (10) to allow a decreased flow of mobile phase from the separator (2) to the detector (4), wherein the pressure restrictor (10) is in fluid communication with the detector (4) and separator (2); and c) deactivating the pump (1) to allow a decreased flow of mobile phase into the separator (2) and to the detector (4).

The embodiments of the methods described above can be combined in any manner. Thus, features from one embodiment can be combined with features from any other embodiment. For example, the embodiments described above can be combined in a manner to produce methods for increasing sensitivity of detection of an analyte comprising: passing a mobile phase comprising the analyte from a separator (2) to a detector (4) at a first detector flow rate, wherein the separator (2) and detector (4) are in fluid communication with each other, wherein the separator (2) is a liquid chromatography column, a high pressure liquid chromatography column, a capillary column, a nano liquid chromatography column, or a reverse phase high pressure liquid chromatography column, and wherein the detector (4) is a mass spectrometer, a nuclear magnetic resonance detector, a radioactivity detector, an ultraviolet detector, or an electrochemical detector; and decreasing the first detector flow rate of the mobile phase through the detector (4) to a second detector flow rate when the signal from the detector (4) is less than a preset threshold or at a predetermined time, wherein the decreasing is carried out by: a) deactivating a volume-adding component (5) such as a second pump, wherein the second pump is in fluid communication with the detector (4) and is located between the detector (4) and the separator (2), whereby the activated second pump reduces the volume of an agent into the mobile phase passing into the detector (4); b) deactivating a pressure restrictor (10) such as a needle valve to allow a decreased flow of mobile phase from the separator (2) to the detector (4), wherein the needle valve is in fluid communication with the detector (4) and separator (2); or c) deactivating a pump (1) to allow a decreased flow of mobile phase into the separator (2) and to the detector (4); or any combination thereof. In some embodiments, the volume-adding component (5), pressure restrictor (10), and pump (1) can be of any type described herein. Further, upon obtaining a signal less than the preset threshold or when reaching a predetermined time, the detector (4) signals a controller (42), which is in electronic communication with the detector (4), as described above, whereby the controller (42) signals the pressure restrictor (10), pump (1), or volume-adding component (5) to introduce less mobile phase passing into the detector (4), thereby decreasing the first detector flow rate to the second detector flow rate. The controller (42) can be any controller described above.

Figure 2:
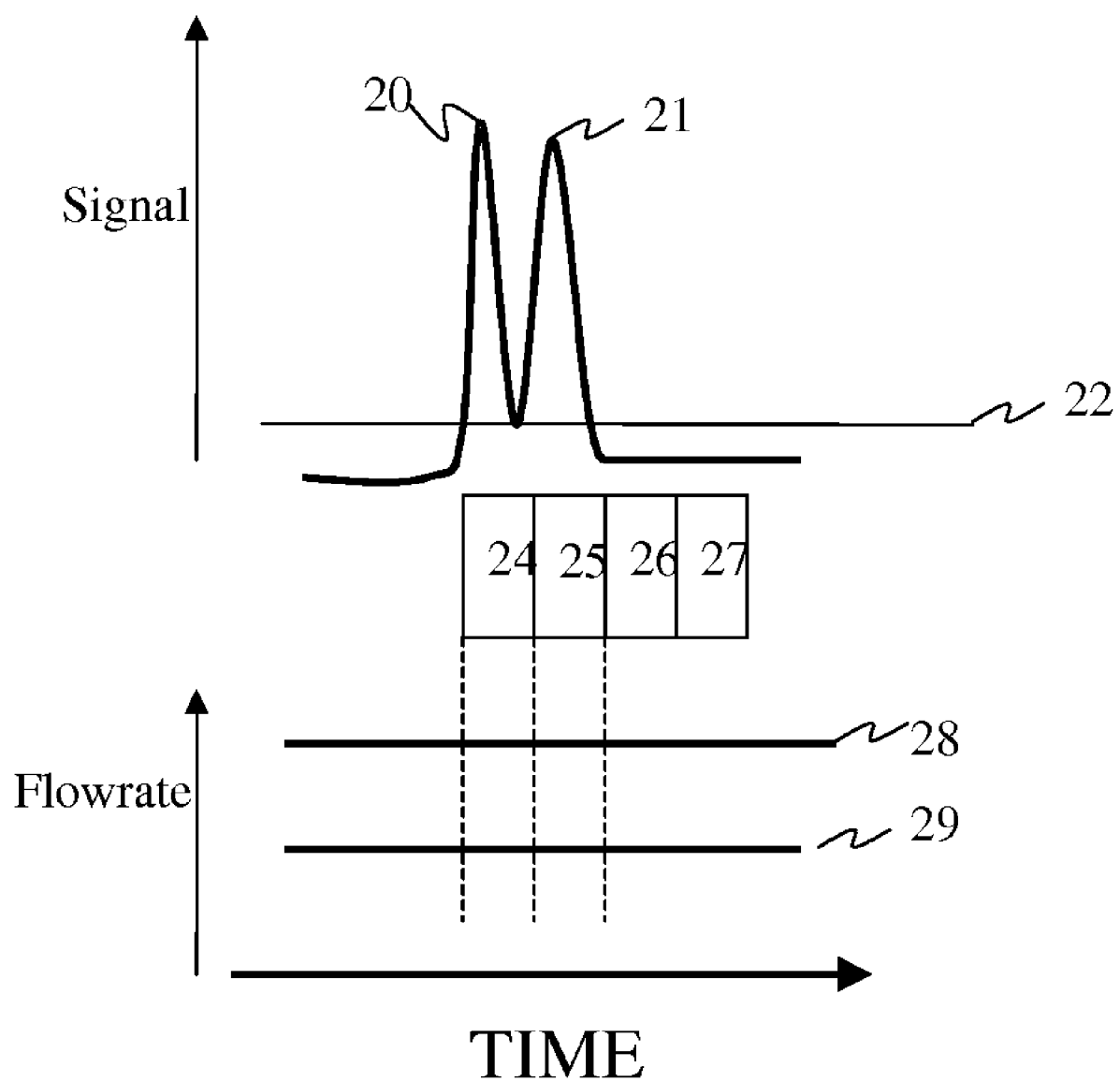
FIG. 2 illustrates chromatographic separation of radioactive peaks without changes in flow rates for both LC and agent using conventional chromatography.
Figure 3:
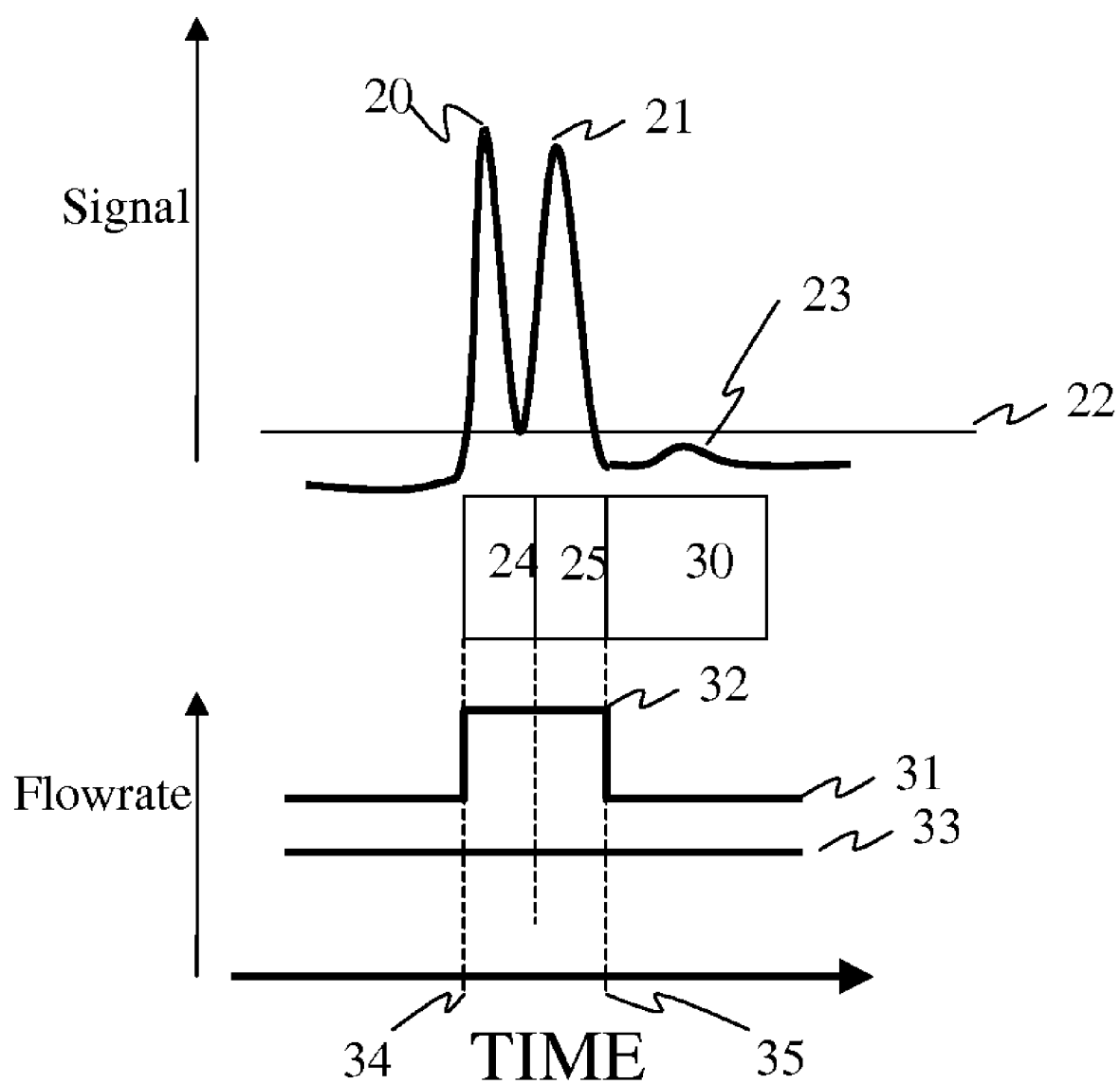
FIG. 3 illustrates detection of a minor radioactive peak with dynamic flow chromatography where the pump changes the flow rate of the agent based on signal level.

A representative implementation of the present invention is shown in FIG. 3. During the analysis, a predefined radioactivity threshold (22) is set. For example, the threshold can be set to 100 CPM (counts per minute). When the signal is below the threshold, the volume-adding component (5), such as a second pump, flows at a lower flowrate (31) (for example, 1 ml/min) for StopFlow™ AD cocktail from AIM Research Co (Hockessin, Del.). When the radioactive signal exceeds the threshold (22) at time point (34), the agent flowrate is increased to a higher flowrate (32) to resolve the peaks (20) and (21) (see, FIG. 2; also see TOFS (24), (25), (26), and (27) for conventional chromatography separation; flow rate of volume-adding component (28); flow rate of pump (29)). For example, the higher flowrate of agent pump can be set to 5 ml/min. The TOF for higher peaks would be 500/1000(1+5)= 5 seconds. This means resolution for higher peaks will be better than the TOF of 7.5 seconds using 3:1 ratio for the entire run.

When the signal becomes below threshold (22) at time point (35), the agent flowrate is reduced down to a lower flowrate (31) again. Time of flight for areas where low radioactivity is detected is indicated (30). Predefined LC flowrate in LC gradient is shown (33). A lower flowrate (31) gives longer TOF of $(500/(1000(1\pm1))\times60)=15$ seconds, which enables the detection of a smaller peak (23) because of longer TOF. This increases the radioactivity detection sensitivity by at least 30%. Under this method, LC flowrate is not changed during the analysis from the predefined gradient table.

Figure 4:
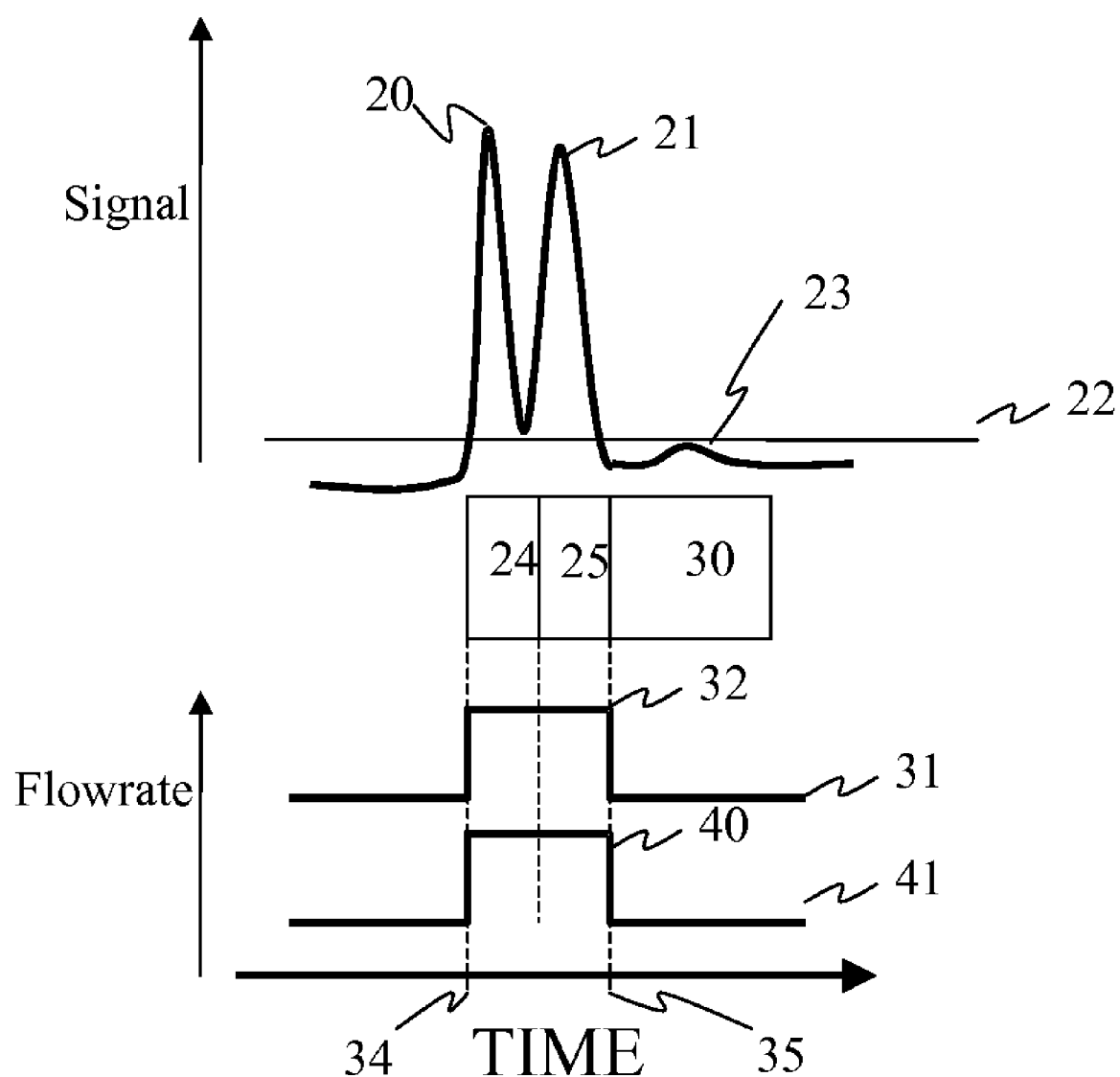
FIG. 4 illustrates detection of a minor radioactive peak with dynamic flow chromatography where both the flow rate of the pump and/or agent vary according to signal level.

FIG. 4 describes another implementation of current invention. In order to give different TOF's for higher and lower peaks, LC (liquid chromatography) flowrate can also be changed based on the signal level. When the radioactive signal exceeds the threshold (22), LC flowrate is increased to a higher level (40) (e.g. 1 ml/min). When the radioactive signal is below the predefined threshold (22), the LC flowrate is kept at lower flowrate (41) (e.g. 0.5 ml/min). This method has same effects on increasing resolution on higher peaks and sensitivity for lower peaks.

Another method of the present invention is to keep agent flow constant and change LC flowrate during the analysis depending on the signal level. In the other words, LC flowrate can be increased when a signal exceeds the threshold (22) and reduced when signal becomes below the threshold. This method also improves resolution for higher peaks and sensitivity for lower peaks as described above. When the method of reducing the LC flowrate is applied for current invention, a pressure restrictor (10) as showed in FIG. 1 can be used to keep the column pressure high. Keeping the column pressure at higher pressure levels will prevent the peaks to broaden during the analyses. For example, if the normal LC gradient is set at 1 ml/min flowrate and the LC pressure is at 150 bar at this flowrate. When the LC flowrate is reduced to a lower flowrate (e.g. 0.25 ml/min), the pressure restrictor (10) closes in to restrict the LC flow so that a similar pressure (e.g. 150 bar) can be kept for the regions where lower LC flowrate is applied.

It should be understood that the embodiments and drawings described herein are only some examples of the apparatus and methods described herein and are not to be construed as limiting the invention in any manner. In addition, various modifications of the invention, in addition to those described herein, will be apparent to those skilled in the art from the foregoing description. Such modifications are also intended to fall within the scope of the appended claims.

What is claimed is:

1. A method for increasing sensitivity of detection of an analyte comprising:
   passing a mobile phase comprising the analyte from a separator to a detector at a first detector flow rate, wherein the separator and detector are in fluid communication with each other; and
   decreasing the first detector flow rate of the mobile phase through the detector to a second detector flow rate when a signal from the detector is less than a preset threshold or when reaching a predetermined time.

2. The method of claim 1 wherein the first detector flow rate is decreased to the second detector flow rate by deactivating a volume-adding component, wherein the volume-adding component is in fluid communication with the detector and is located between the detector and the separator, whereby the activated volume-adding component reduces the volume of an agent into the mobile phase passing into the detector.

3. The method of claim 2 wherein the volume-adding component is a second pump.

4. The method of claim 2 wherein the agent is a second mobile phase, a scintillation fluid, or an organic solvent.

5. The method of claim 2 wherein a controller, which is in electronic communication with the detector and volume-adding component, deactivates the volume-adding component.

6. The method of claim 1 wherein the first detector flow rate is decreased to the second detector flow rate by any combination of:
   deactivating a volume-adding component, wherein the volume-adding component is in fluid communication with the detector and is located between the detector and the separator, whereby the activated volume-adding component reduces the volume of an agent into the mobile phase passing into the detector;
   deactivating a pressure restrictor to allow a decreased flow of mobile phase from the separator to the detector, wherein the pressure restrictor is in fluid communication with the detector and separator; and
   deactivating a pump, wherein the pump is in fluid communication with the separator, to allow a decreased flow of mobile phase into the separator and to the detector.

7. The method of claim 6 wherein the pressure in the separator remains substantially steady after a first restrictor flow rate is decreased to a second restrictor flow rate.

8. The method of claim 6 wherein the separator is a liquid chromatography column, a high pressure liquid chromatography column, a capillary column, a nano liquid chromatography column, or a reverse phase high pressure liquid chromatography column, the pressure restrictor is a needle valve, and the volume-adding component is a second pump.

9. The method of claim 6 wherein a controller, which is in electronic communication with the detector and pressure restrictor, deactivates the pressure restrictor.

10. The method of claim 6 wherein a controller, which is in electronic communication with the detector and the pump, deactivates the pump.

11. The method of claim 1 wherein the second detector flow rate is at least about 100% slower than the first detector flow rate.

12. The method of claim 1 wherein the second detector flow rate is at least about 1000% slower than the first detector flow rate.

13. The method of claim 1 wherein the second detector flow rate is at least about 20,000% slower than the first detector flow rate.

14. The method of claim 1 wherein the detector is a mass spectrometer, a nuclear magnetic resonance detector, a radioactivity detector, an ultraviolet detector, or an electrochemical detector.

15. A method for increasing sensitivity of detection of an analyte comprising:
   passing a mobile phase comprising the analyte from a pump to a separator to a detector at a first detector flow rate, wherein the separator and detector are in fluid communication with each other, wherein the separator is a liquid chromatography column, a high pressure liquid chromatography column, a capillary column, a nano liquid chromatography column, or a reverse phase high pressure liquid chromatography column, and wherein the detector is a mass spectrometer, a nuclear magnetic resonance detector, a radioactivity detector, an ultraviolet detector, or an electrochemical detector; and
   decreasing the first detector flow rate of the mobile phase through the detector to a second detector flow rate when a signal from the detector is less than a preset threshold or at a predetermined time, wherein the decreasing is carried out by:
   deactivating a second pump, wherein the second pump is in fluid communication with the detector and is located between the detector and the separator, whereby the activated second pump reduces the volume of an agent into the mobile phase passing into the detector;
   deactivating a needle valve to allow a decreased flow of mobile phase from the separator to the detector, wherein the needle valve is in fluid communication with the detector and separator; or
   deactivating the pump to allow a decreased flow of mobile phase into the separator and to the detector;
   or any combination thereof.

16. The method of claim 15 wherein the pressure in the separator remains substantially steady after a first restrictor flow rate in the needle valve is decreased to a second restrictor flow rate.

* * * * *